United States Patent [19]
Palmer et al.

[11] Patent Number: 5,112,741
[45] Date of Patent: May 12, 1992

[54] ACETALDEHYDE TRAPPING SYSTEM

[75] Inventors: John L. Palmer, Philadelphia; Marsha W. Timmerman; Stephan D. Daubney, both of Allentown, all of Pa.

[73] Assignee: Enzymatics, Inc., Horsham, Pa.

[21] Appl. No.: 216,008

[22] Filed: Jul. 7, 1988

[51] Int. Cl.$^5$ .............................................. C12Q 1/26
[52] U.S. Cl. ........................................ 435/25; 435/26; 436/131; 436/132
[58] Field of Search ................... 435/26, 25, 805, 810; 436/175, 106, 111

[56] References Cited

U.S. PATENT DOCUMENTS 3,493,467  2/1970  Drell et al. ............................ 435/26
4,786,596 11/1988  Adams ................................... 435/25

OTHER PUBLICATIONS

Poklis and Mackell *Clin. Chem.* 28:2125, 1982.

*Primary Examiner*—Sam Rosen
*Attorney, Agent, or Firm*—Finnegan, Henderson, Farabow, Garrett & Dunner

[57] ABSTRACT

The invention provides a reagent system for the enzymatic determination of an oxidizable substrate in a fluid sample; the system includes an active amine trap for inactivating high concentrations of aldehyde and ketone oxidation products comprising a combination of at least one primary amine and at least one alpha-effect amine. An example of the oxidizable substrate is alcohol.

33 Claims, No Drawings

ACETALDEHYDE TRAPPING SYSTEM

BACKGROUND OF THE INVENTION

1. Field of the Invention

Diagnostic procedures based on the enzymatic determination of substances in biological fluids are well-known. In the enzymatic determination of alcohol or other dehydrogenase/oxidase substrates in body fluids, enzyme assay systems comprising a dehydrogenase and a cofactor for the enzyme (usually NAD+) are typically employed to oxidize the substrate and simultaneously reduce the cofactor to a readily assayable product.

In the case of an alcohol, selective oxidation by such enzyme systems results in the production of the corresponding free aldehyde or ketone. The presence of these oxidation products are very detrimental to the assay, as firstly, they tend to inactivate the enzymes employed in the system, and, secondly, they unfavorably shift the dehydrogenation reaction equilibrium so that oxidation of the substrate does not tend to go to completion. Since assay results under these conditions are unreliable, enzyme assay systems for the determination of alcohol now typically require dilution of the substrate and/or include complexing or trapping agents for the oxidation products which in essence remove free aldehyde or ketone from the reaction.

2. Description of Related Art

A variety of agents for trapping alcohol oxidation products, especially acetaldehyde produced by enzymatic dehydrogenation of ethanol, have been proposed. In commercial applications, the class of agents generally employed comprises primary amines, which react with free aldehyde to form the corresponding imine. Since the product imine is less reactive than the precursor aldehyde or ketone, enzyme deactivation is reduced, and the dehydrogenation reaction equilibrium is favorably shifted. Even with the primary amine trapping agents, however, the alcohol dehydrogenation typically still does not go substantially to completion, with often less than about 20% of the alcohol converted. Further, assay systems employing a primary amine as trapping agent for alcohol oxidation products are generally only useful for assaying fluids having a low alcohol content and a correspondingly low production of aldehyde or ketone oxidation product. In general, the usefulness of these enzyme assay systems is limited to samples producing less than about 5 mM acetaldehyde, more typically less than about 1 mM acetaldehyde, as the known primary amine trapping agents cannot effectively remove larger amounts from the assay system. For instance, acetaldehyde in concentration greater than 1 mM inhibits the enzyme alcohol dehydrogenase (ADH). Since analysis of body fluid samples potentially containing in excess of about 150 mM alcohol is routine, such samples must be diluted prior to assay to reduce target concentrations to an assayable level. For example, in situations where 21 mM blood ethanol is the legal definition of intoxication, and the sample is to be tested for this concentration, the sample must be diluted sufficiently to reduce the alcohol concentration thereof to within the assay range; generally to less than about 5 mM, depending upon the particular assay system. This must be done very carefully to ensure an accurate determination.

An example of known systems is the Abbott TDX Analyzer. This device requires extensive dilution of the sample to be tested so that only 1 mM of acetaldehyde is produced since otherwise the undesirable results discussed above will take place. The Abbott Analyzer uses an acetaldehyde trap, 2-amino-2-methyl-1,3-propanediol ("Tris amino" or "Tris") as a buffer.

Another illustration of this type of assay is illustrated by U.S. Pat. No. 3,926,736 to Buccolo (Calbiochem), 1975. The patent discloses the use of Tris buffer as a trapping agent. The samples to be analyzed are diluted so that only about 0.5 mM acetaldehyde is produced.

U.S. Pat. No. 4,481,292 to Raymond (The Coca-Cola Company), 1984, also shows the use of Tris buffer as trapping agent for high concentrations of acetaldehyde. The reactor is adapted for and the process is a continuous flow type.

The patent describes the difficulties encountered in a practical enzyme-catalyzed process for converting ethanol to acetaldehyde, including equilibrium considerations which favor acetaldehyde conversion to alcohol. Although concentrations of acetaldehyde on the order of 85 mM are disclosed, it is essential in accordance with the process (and apparatus) that the alcohol dehydrogenase (ADH) be separated and confined during the reaction sequence. The ADH is separated by a semipermeable membrane from the acetaldehyde and the system permits the passage of the starting materials as well as the products formed so that a liquid flow away from the enzyme takes place on a continuous basis. Thus, the enzyme is never exposed to high concentrations of acetaldehyde. Even under such conditions, the yield of acetaldehyde is quite limited, the conversion of the alcohol being about 18%. The efficiency of the amine buffer system is not a feature of the process, and "Tris" is not capable by itself of reacting with and removing such high concentrations of acetaldehyde.

The process and the system of the present invention does not call for a flow system, twice the amount of acetaldehyde can be trapped and 100% of the alcohol can be converted to acetaldehyde.

The system of the invention can be embodied and used as a dry film rather than a large continuous flow reactor. Other differences between the device of the invention and the prior art will become apparent in the description of the invention as presented herein.

Owing to the inability of these known systems to assay for routinely encountered concentrations of alcohols without sample dilution, the assay is of necessity a liquid assay with the reagents supplied in liquid form, usually as a kit. Sigma Chemical, for example, markets the following individual liquid reagents for the enzymatic determination of ethyl alcohol in blood samples: NAD-ADH; ethanol standard solution; hydrazine; glycine buffer reagent; trichloroacetic acid solution. These liquid reagents are bulky, and must be carefully combined in the proper amounts for each assay, refrigerated during storage, and protected against contamination and spillage.

Bostick and Overton (*Biotechnol. Bioengin.* 22:2383-92, 1980) also describe the addition of hydrazine to an enzymatic alcohol test, which increases the effectiveness of the measuring range to 3 mM, and the test format is liquid.

In *Biochem. J.*, 104 p. 165 (1967), Dickinson and Dalziel, The Specificities and Configurations of Ternary Complexes of Yeast and Liver Alcohol Dehydrogenases, discuss the use of Tris as an acetaldehyde trapping agent. The authors note that Tris is an unsuitable buffer for equilibrium or initial-rate measurements with some carbonyl compounds. The authors state, however, that Tris does not afford a convenient buffer for the enzymatic estimation of small amounts of ethanol. Additional differences over that art will become apparent from the detailed discussions which follow.

It is accordingly desirable and there is a need to provide an assay in a fluid for the enzymatic determination of alcohol concentration, which is capable of reliably converting substantially 100% of the substrate, trapping high concentrations of ketone or aldehyde (in excess of 5 mM, e.g. in excess of 150 mM), does not deactivate enzyme reagents, is useful for determining high alcohol concentrations without sample dilution (e.g. in the range of 20 to 150 mM, or higher), which can be provided in easily useable and storable form such as a dry film format, and which is highly reliable in use, even for inexperienced assayers.

SUMMARY OF THE INVENTION

The invention provides an assay for the enzymatic determination of the alcohol content of a fluid, particularly a body fluid of a mammal, based on enzyme-catalyzed oxidation of the alcohol present to a corresponding aldehyde or ketone (generically "carbonyl compound"), with simultaneous reduction of NAD+ to NADH. The assay includes a reagent system preferably comprising NAD+, alcohol dehydrogenase (ADH), buffering agent, and a non-volatile trapping agent for the alcohol dehydrogenation product. In a particular embodiment, the invention provides a diagnostic kit comprising a film-forming reagent system including a marker for NADH, applied to support means for physically supporting the film. An ideal embodiment is a dry film.

It is also envisioned that this trapping system can be used with other enzyme systems which oxidize alcohol to form inactivating carbonyl compounds, for example oxidase enzymes, and for a specific example, alcohol oxidase, which will convert methanol and ethanol to the inactivating respective carbonyl compounds, formaldehyde and acetaldehyde.

The trapping agent is selected for non-volatility, good solubility, and effective, preferably substantially complete, inactivation of the dehydrogenation product, at sample alcohol concentrations up to about 200 mM. With appropriate selection of trapping agent, the assay provides reliable end-point determinations (alcohol conversion of about 100%), even at high alcohol concentrations, and full enzyme activity over the course of the reaction.

In the below-described invention, the term cofactor describes any second substrate to the enzyme oxidase on dehydrogenase which is capable of accepting electrons derived upon oxidation of the first substrate, such oxidation of the first substrate resulting in production of a ketone or aldehyde.

DETAILED DESCRIPTION OF THE INVENTION

The assay method of the invention is based on known assays wherein the alcohol content of a fluid sample is enzymatically determined by enzyme-catalyzed oxidation of the alcohol employing a reagent system including a dehydrogenase or oxidase and a cofactor for the enzyme which is simultaneously reduced as the alcohol is oxidized; the amount of reduced cofactor present in the sample after completion of the reaction is then determined, typically by colorimetric analysis; the amount of alcohol originally present in the sample may be determined against a standard for the analysis, or a simple end-point determination employed.

The basic principles of this reaction are well-known, as discussed above, and the general process is widely used for the determination of ethanol content of blood or saliva. Typically, the ethanol content of the sample is dehydrogenated in the presence of ADH, which is a highly specific enzyme for this reaction. The reducible cofactor employed is usually NAD+, which is simultaneously reduced as the ethanol is oxidized on a mole equivalent basis. The amount of ADH employed is an amount sufficient to obtain the desired sample enzyme activity, and sufficient NAD+ is employed to ensure that the reaction goes to completion. The known systems are conventionally buffered to a pH which promotes maximum enzyme activity.

In accordance with the present invention, the reagent system for the enzymatic determination of alcohol further includes a trapping system for trapping and removing aldehyde or ketone oxidation products from the reaction mixture comprising a non-volatile active amine trap including at least one primary amine and at least one alpha-effect amine, wherein each of the amines is a) non-volatile and b) characterized by a pKa of at least about 7.5. Though the independent use of alpha-effect amines as aldehyde traps in kinetic reactions is known in the art, the end product (e.g. the aldehyde) is present in low concentrations generally below 5 mM, commonly below 1 mM. The results obtained by the us of the amines in combination in accordance with the invention as described herein is quite unexpected.

For reasons which are not well understood at the present time, the use of a combination of alpha-effect and primary amines according to the present invention dramatically increases the aldehyde/ketone trapping capacity of the amine trap, as compared to prior art amine traps consisting essentially of primary amine or of alpha-effect amine. Increases in trapping capacity, as measured by effective inactivation of aldehyde/ketone oxidation product in the reaction mixture, of up to about 100-fold over known prior art traps are typical. Since alpha-effect amines do not function well alone as traps in standard ethanol ADH/NAD+ reaction systems, and primary amines alone have a limited trapping capacity in such systems, it is postulated that the primary amine according to the present invention catalyzes or otherwise activates the alpha-effect amine trapping function, and that the alpha-effect amine is the ultimate trap.

Primary and alpha-effect amines suitable for use in the practice of the present invention are selected for their non-volatility, pKa, solubility, and ability to function in combination as an active amine trap in enzymatic determinations of alcohol according to the invention at the biological pH range of the enzyme, without denaturation or substantial deactivation of the enzyme. An "active amine trap" according to the present invention is a trap capable of substantially inactivating at least about 5 mM acetaldehyde from a standard enzyme-catalyzed oxidation of ethanol employing an ADH/NAD+ reagent system; preferably the trap is capable of substantially inactivating at least about 20 mM acetaldehyde from this system, and more preferably, at least about 50 mM acetaldehyde. Removal of acetaldehyde up to about 150 mM concentrations and greater, are contemplated. It is noted that, while the term "active amine trap" is defined herein with reference to an ADH/NAD+ reagent system with ethanol as the substrate, the broad use of the active amine trap of the invention in a range of enzymatic determinations of alcohols or other enzymatically oxidizable substrates producing aldehyde or ketone oxidation products, such as acids, is contemplated.

With proper selection of amines, typical substrate conversions of about 100% are obtainable without dilution of the sample alcohol concentrations up to about 150 mM, thus permitting accurate and reliable end-point determinations. Such conversions are obtained by selection of amines for trap efficiency so that accumulation of active oxidation product is avoided. This ensures that a favorable reaction equilibrium is established, and that the catalyzing enzyme is not deactivated by oxidation product; the use of amines in the practice of the invention which tend to deactivate the catalyzing enzyme should, of course, be avoided.

The amines employed in the active amine trap of the invention are preferably substantially non-volatile amines having a boiling point above about 200° C. (1 atm), a molecular weight greater than about 150, or both. However, in some instances, slightly more volatile amines may be employed, as long as the trapping combination of amines is substantially non-volatile (bp>200° C. at 1 atm). Preferably, the amines employed have a high solubility, preferably at least a solubility in water of at least about 100 mM at room temperature (25° C.).

Non-volatile amines having the requisite pKa useful in the practice of the present invention are conveniently and easily selected from such known prior art amines. Exemplary suitable primary amines for use in the present invention comprise amines of the following categories having the pKa, volatility, and solubility characteristics described above and carrying at least one primary amino substituent:

1) unsubstituted or substituted naturally-occurring amino acids such as lysine, arginine, alanine, serine, proline, glycine, glycylglycine, and glycine methyl or ethyl ester;

2) non-naturally occurring amino acids, such as amino $C_2$–$C_{10}$-carboxylic acids, particularly aminobutyric acid or aminocaprylic acid;

3) compounds containing both a primary amino substituent and a non-carboxy acid-functional moiety, such as amino-$C_1$–$C_{10}$-alkyl-substituted inorganic acids, particularly aminoethyl phosphoric acid or aminoethyl sulfonic acid;

4) compounds containing a primary amino substituent and an additional functional group bearing a fixed charge, such as amino-tetraalkylammonium salts or amino-tetraalkylphosphonium salts;

5) primary amines having a molecular weight of more than about 150 or a boiling point greater than about 200° C. (at 1 atm), or both, and which are accordingly substantially non-volatile, such as $C_8$–$C_{20}$-alkyl or -cycloalkyl-amines, or $C_6$–$C_{20}$-alkylenediamines such as 1,6-diaminohexane; and 6) primary amines containing hydrogen bonding sites which act to increase their boiling point and render them non-volatile, such as Tris hydroxyl methylamine methane.

Alpha-effect amines and their use as aldehyde traps in kinetic studies is known in the art, as described, for example, in a report by W. P. Jencks, *Catalysis in Chemistry and Enzymology*, McGraw Hill, N.Y. (1969), incorporated herein by reference. Suitable exemplary alpha-effect amines for use in the practice of the present invention comprise alpha-effect amines of the following categories having the pKa, volatility, and solubility characteristics set forth above:

1) substituted $C_2$–$C_8$-hydrazines such as carboxymethylhydrazine, nitrophenyl hydrazine, ethylhydrazine acetate, 2-hydrazine-2-imidazole, and 1,3-dihydroxyl-2-hydrazinopropane; and 2) substituted $C_2$–$C_8$-alkylhydroxylamines, including salts thereof, such as carboxymethoxyamine salts, carboxy-$C_2$–$C_8$-alkylhydroxyl-amines, benzylhydroxylamine, and substituted benzylhydroxyl-amines, especially nitrobenzylhydroxylamines.

Generally, alpha-effect hydroxylamines suitable for use in the practice of the invention comprise hydroxylamines containing at least 2 carbon atoms (i.e., are substantially non-volatile), and have at least two hydroxyl substituents (i.e., have good solubility).

Again, alpha-effect and primary amines useful in the practice of the present invention are readily identified by one of ordinary skill in the art, for example by reference to any standard text such as the *Chemistry and Physics, CRC Press* for pKa, solubility, and volatility characteristics. The ratio of primary amine to alpha-effect amine in the amine trap is not critical, as long as the activity of the trap meets the above-specified parameters. Generally, however, at least about 10% w/w of total primary amine to total alpha effect amine is employed, and preferably no more than about 60% w/w primary amine. A range of from about 20% by weight to about 50% by weight total primary amine, based on the weight of total alpha-effect amine, is most preferred.

In a further embodiment of the invention, it has been discovered unexpectedly that a suitable trap for the practice of the invention can be the diamine, 1,6-hexanediamine. This diamine can be used alone without the alpha-effect amine. For reasons which are not well understood at the present time, very satisfactory results are obtained by the use of this diamine alone as trapping agent according to the invention. However, this diamine may also be used with at least one other primary amine as described above. Generally, 1,6-hexanediamine is used as the active amine trap of the invention in an amount ranging from about 20% by weight up to 100% by weight, based on the total weight of amines present.

In the practice of the process of the invention, the active amine trap is added to a conventional reaction system comprising a dehydrogenase or oxidase, a reducible cofactor, and an alcohol substrate for the enzyme, in an amount which will substantially inactivate alcohol oxidation product and remove it as a reactant from the system. Generally a concentration of primary amine plus alpha-effect amine, or 1,6-hexanediamine plus additional primary amine if used, of at least about 4 times that of the alcohol substrate is effective to achieve maximum trap activity. Lower amine concentrations of at least about 1.5 times that of the substrate concentration may, however, be effective in particular applications. Excess amine does not appear to generally adversely affect the reaction. Preferably, the reaction mixture is buffered to between about pH 9 and 10, which maximizes the extent and rate of the reaction, without substantially inhibiting enzyme activity.

The concentration of alcohol in the sample is conveniently determined by colorimetric quantitation of reduced cofactor, according to conventional processes.

Typically, NADH is determined by ultraviolet colorimetry at 340 nm, at which wavelength NADH absorbs ultraviolet light, but NAD does not. Alternatively, markers for NADH which allow the quantitative determination thereof are employed, typically chromogens reactive with NADH.

In a preferred embodiment of the invention, the reagent system of the invention for the enzymatic determination of alcohol is disposed as a film on a solid support, and dried. Owing to the low volatility of the amine trap, the trapping system of the invention is retained as a film-forming component, without evaporation during the drying process. To use, a fluid sample is placed in contact with the dried reagent film, and the alcohol content of the sample determined by quantitating reduced cofactor present, preferably NADH, typically by colorimetric analysis. Conveniently, the reagent system includes a chromogen quantitatively reactive with the reducible cofactor, and the chromogen/cofactor product is either quantitated against a standard to determine alcohol content of the sample, or is selected to provide an end-point determination, as known in the art and as described, for example, in U.S. patent applications Ser. Nos. 943,414 and 075,817, of common assignment herewith, and incorporated herein by reference.

Suitable solid supports are also described at length in these applications, and include sheets, rods, webs, sticks, or strips of paper, glass, cellulose, wood, metal, or polymers such as polyalkylenes or polycarbonates. In a particularly preferred embodiment, a bibulous material such as filter or blotting paper capable of adsorbing a fixed amount of liquid per unit is incorporated into the reagent system in a predetermined amount to thereby provide a standardized sample for enzymatic determination according to the invention.

The components of the assay system of the invention are preferably prepared in a liquid form for deposit upon the support member. Once placed on the support member, the components in solution are dried to adhere the compositions to the support member. Generally, adhesion of the reactant compositions to the support member is conveniently effected when the support member is a bibulous material. Certain binders such as resin or gums are advantageously incorporated into the reactant compositions to assist in adhering them to non-porous support members such as metal, glass or non-porous polymeric materials. Conventionally employed inert filters, binders, surfactants and the like may also be incorporated into the reagent compositions when desired. The assay device is preferably kept under conditions that do not cause the deactivation of the enzyme, e.g. avoiding high temperature.

The following Examples illustrate the invention and are not intended to be a limitation in any way whatever.

EXAMPLE 1

To a reaction mixture containing 5 IU ADH, 100 mM NAD, pH 9.5 and 65 mM ethanol was added a trapping mixture containing:
  400 mM Tris, pH 9.5
  200 mM Glycine, pH 9.5
  50 mM Carboxymethoxyamine, pH 10
All of the alcohol was oxidized to produce 65 mM acetaldehyde and NADH. When 650 mM borate buffer was substituted for the amine containing buffers listed above, less than 4 mM of alcohol was oxidized, and the ADH enzyme was inactivated by the free aldehyde present in the reaction. Use of 650 mM of Tris buffer in the absence of alpha-effect amine did not result in complete alcohol oxidation. Use of 650 mM carboxymethoxyamine and borate buffer, without added primary amine, again did not result in the complete oxidation of the alcohol.

EXAMPLE 2

A trapping mixture containing:
120 mM Tris, pH 9.5
120 mM Glycine, pH 9.8
150 mM Carboxymethoxyamine, pH 10
was substituted for the trap in Example 1. Identical results were obtained.

EXAMPLE 3

A trapping mixture containing:
100 mM Hexanediamine, pH 10
100 mM Glycine, pH 9.8
150 mM Carboxymethoxyamine, pH 10
was substituted for the trap in Example 1. Identical results were obtained.

EXAMPLE 4

A trapping mixture containing:
120 mM Tris, pH 9.5
120 mM Glycine, pH 9.8
150 mM Allylhydroxylamine, pH 9.8
was substituted for the trap in Example 1. Identical results were obtained.

EXAMPLE 5

A trapping mixture containing:
120 mM Tris, pH 9.8
120 mM Glycine, pH 9.8
100 mM Nitrobenzylhydroxylamine, pH 10
was substituted for the trap in Example 1. Identical results were obtained.

EXAMPLE 6

To a reaction mixture containing 5 IU/ml ADH, 200 mM NAD pH 9.5, and 150 mM ethanol was added a trapping formulation containing:
240 mM Tris, pH 9.8
240 mM Glycine, pH 10
200 mM Carboxymethoxyamine, pH 10
Complete oxidation of all of the alcohol was observed, indicating that this formulation was capable of trapping 150 mM of acetaldehyde. Once again, elimination of either the primary amine or the alpha-effect amine resulted in failure to observe complete alcohol oxidation. This failure was not due to lack of sufficient buffer, as the addition of a non-amine containing borate buffer did not result in complete oxidation.

EXAMPLE 7

To the reaction mixture described in Example 6 was added:
120 mM Hexanediamine, pH 10
200 mM Glycine, pH 10
200 mM Carboxymethoxyamine, pH 10

EXAMPLE 8

To the reaction mixture described in Example 6 was added:
100 mM Hexanediamine, pH 9.8
200 mM Glycine, pH 10
120 mM Nitrobenzylhydroxylamine, pH 10

Identical results as described in Example 6 were observed.

EXAMPLE 9

The combined reaction and trapping mixtures of Example 1, further including 1 mM MTT chromogen [2-(2¹-triazolyl)-3,5-diphenyl tetrazolium bromide], are applied to an absorbent paper in an amount sufficient to saturate the paper. The paper is then dried and cut into 0.5 inch diameter circles. To all but one of the circles, 20 ul of fluid sample containing unknown concentrations of ethanol are applied; the remaining circle serves as a control. A color change from the pale yellow shade of the control paper to a bright blue in the presence of the sample fluid indicates a sample alcohol concentration of at least 20 mM alcohol.

The relative equilibrium constants for trapping agents are listed below in Table 1.

Their relative equilibrium constants were determined by measuring the NADH production by alcohol dehydrogenase after 10 minutes in the presence of each of the trapping agents.

The reaction formulation was as follows:
200 mM Glycine, pH 9.5, primary amine
10 mM NAD
5 mM ethanol
5 mM trapping agent
125 IU ADH

TABLE 1

| TRAP | RELATIVE EQUILIBRIUM CONSTANT |
|---|---|
| Control (no trapping agent) | .05 |
| Methoxyamine | 11.7 |
| Ethylhydroxylamine | 11.8 |
| Tris | .2 |
| Nitrobenzylhydroxylamine | 202.0 |
| O-Benzylhydroxylamine | 40.9 |
| Carboxymethoxyamine | 38.6 |
| Allylhydroxylamine | 25.3 |

We claim:

1. A method for trapping an aldehyde or ketone in an assay for alcohol comprising:
    reacting an active amine trap comprising a combination of at least one alpha-effect amine and at least one primary amine, wherein each of the amines employed is substantially non-volatile and has a pKa of at least about 7.5, with
    a fluid sample comprising an aldehyde or ketone which is an oxidation product of an enzymatic oxidation reaction of an enzyme substrate, wherein the concentration of said enzyme substrate and oxidation product is greater than about 5 mM.

2. The method of claim 1, wherein each of the amines employed has a solubility in water at 25° C. of at least about 100 mM.

3. The method of claim 1, wherein the active amine trap is capable of inactivating a concentration of aldehyde o ketone oxidation product of at least about 20 mM.

4. The method of claim 1, wherein the active amine trap is capable of inactivating a concentration of aldehyde or ketone oxidation product of at least about 50 mM.

5. The method of claim 1, wherein the active amine trap is capable of inactivating a concentration of aldehyde or ketone oxidation product of about 150 mM.

6. The method of claim 1, wherein the alpha-effect amine is a substituted hydrazine or substituted hydroxylamine.

7. The method of claim 1, wherein the primary amine is a naturally-occurring amino acid or a non-naturally occurring amino acid comprising an amino-$C_2$-$C_{10}$-carboxylic acid.

8. The method of claim 1, wherein the weight ratio of primary amine to alpha-effect amine is from about 10% w/w to about 60% w/w.

9. The method of claim 6, wherein the weight ratio is from about 20% w/w to about 50% w/w.

10. The method of claim 1, wherein the dehydrogenation or oxidation takes place at a pH of from about 9 to 10.

11. The method of claim 1, wherein the fluid sample comprising the aldehyde or ketone is a biological fluid.

12. The method of claim 11, wherein the biological fluid is blood or saliva.

13. The method of claim 11, wherein the enzyme substrate is an alcohol.

14. The method of claim 13, wherein the alcohol concentration is up to about 150 mM.

15. The method of claim 14, wherein the conversion rate of the alcohol to ketone product is about 20%.

16. The method of claim 14, wherein the conversion rate of the alcohol to ketone product is about 20 to about 100%.

17. A reagent system for trapping an aldehyde or ketone in an assay for alcohol comprising:
    an active amine trap comprising a combination of at least one alpha-effect amine and at least one primary amine, wherein each of the amines employed is substantially non-volatile and has a pKa of at least about 7.5; and
    a fluid sample comprising an aldehyde or ketone which is an oxidation product of an enzymatic oxidation reaction of an enzyme substrate, wherein the substrate and oxidation product are present in a concentration greater than about 5 mM.

18. The reagent system of claim 17, wherein each of the amines employed has a solubility in water at 25° C. of at least about 100 mM.

19. The reagent system of claim 17, wherein the active amine trap is capable of inactivating a concentration of aldehyde or ketone oxidation product of at least about 20 mM.

20. The reagent system of claim 17, wherein the active amine trap is capable of inactivating a concentration of aldehyde or ketone oxidation product of at least about 50 mM.

21. The reagent system of claim 17, wherein the active amine trap is capable of inactivating a concentration of aldehyde or ketone oxidation product of about 150 mM.

22. The reagent system of claim 17, wherein the alpha-effect amine is a substituted hydrazine or substituted hydroxylamine.

23. The reagent system of claim 17, wherein the primary amine is a naturally-occurring amino acid or a non-naturally occurring amino acid comprising an amino-$C_2$-$C_{10}$-carboxylic acid.

24. The reagent system of claim 17, wherein the weight ratio of primary amine to alpha-effect amine is from about 10% w/w to about 60% w/w.

25. The reagent system of claim 17, wherein the weight ratio is from about 20% w/w to about 50% w/w.

26. The reagent system of claim 17 which is buffered to a pH of from about 9 to 10.

27. The reagent system of claim 17, wherein the enzyme substrate is an alcohol.

28. The reagent system of claim 27, wherein the alcohol concentration is up to about 150 mM.

29. A diagnostic kit for the enzymatic determination of an alcohol in a fluid sample, comprising a film of the reagent system of claim 17 disposed on support means for supporting the film.

30. The diagnostic kit of claim 29, wherein the enzyme substrate is an alcohol.

31. The diagnostic kit of claim 27, wherein the alcohol is ethanol.

32. The diagnostic kit of claim 31, wherein the alcohol concentration is up to about 150 mM.

33. The diagnostic kit of claim 29, wherein the fluid sample comprising the aldehyde or ketone is disposed on a dry physical support.

* * * * *